（12) United States Patent
Reitan et al.

(10) Patent No.: US 8,727,959 B2
(45) Date of Patent: *May 20, 2014

(54) CATHETER PUMP FOR CIRCULATORY SUPPORT

(75) Inventors: Oeyvind Reitan, Lund (SE); Klaus Epple, Rangendingen (DE)

(73) Assignee: Cardiobridge GmbH, Hechingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/186,856

(22) Filed: Jul. 20, 2011

(65) Prior Publication Data

US 2011/0282128 A1 Nov. 17, 2011

Related U.S. Application Data

(62) Division of application No. 12/937,906, filed as application No. PCT/SE2009/000318 on Jun. 22, 2009, now Pat. No. 8,579,858.

(30) Foreign Application Priority Data

Jun. 23, 2008 (SE) ........................................ 0801459
Jun. 23, 2008 (SE) ........................................ 0801460

(51) Int. Cl.
*A61M 1/12* (2006.01)
(52) U.S. Cl.
CPC ........... *A61M 1/12* (2013.01); *A61M 2001/125* (2013.01)
USPC ............................................ 600/16; 604/151
(58) Field of Classification Search
USPC .......................................... 600/16; 604/891.1
See application file for complete search history.

(56) References Cited

U.S. PATENT DOCUMENTS 5,169,378 A 12/1992 Figuera
5,749,855 A 5/1998 Reitan
(Continued)

FOREIGN PATENT DOCUMENTS

EP 0364293 4/1990
EP 0480102 4/1992
(Continued)

OTHER PUBLICATIONS

International Search Report and Written Opinion, dated Oct. 21, 2009 (14 pages).
(Continued)

*Primary Examiner* — Carl H Layno
*Assistant Examiner* — Jon Eric C Morales
(74) *Attorney, Agent, or Firm* — Michael Best & Friedrich LLP

(57) ABSTRACT

A catheter pump intended to be inserted in the circulatory system, for example for assisting the heart, including a hollow catheter, a sheath, a drive cable, a drive shaft, a propeller, a proximal housing, a distal housing, and several filaments. Axial movement of the sheath in relation to the catheter brings the distal housing closer to the proximal housing so that said filaments are unfolded to form a cage. The propeller is pivotable between a first folded position, in which the propeller is parallel with the drive shaft and an unfolded position in which the propeller is perpendicular to the drive shaft. Axial movement of the sheath in a first movement unfolds the cage and in a second subsequent movement, actuation pins of the sleeve act upon a cam surface that unfolds the propeller.

12 Claims, 21 Drawing Sheets

(56) References Cited

U.S. PATENT DOCUMENTS

| | | | |
|---|---|---|---|
| 6,217,541 | B1 | 4/2001 | Yu |
| 2003/0135086 | A1 | 7/2003 | Khaw et al. |
| 2008/0114339 | A1* | 5/2008 | McBride et al. ............ 604/891.1 |
| 2008/0132748 | A1* | 6/2008 | Shifflette ......................... 600/16 |
| 2011/0034874 | A1* | 2/2011 | Reitan et al. .................. 604/151 |

FOREIGN PATENT DOCUMENTS

| | | |
|---|---|---|
| JP | 2008500512 | 1/2008 |
| JP | 2009530041 | 8/2009 |
| WO | 8501436 | 4/1985 |
| WO | 9405347 | 3/1994 |
| WO | 9944651 | 12/1999 |
| WO | 03103745 | 12/2003 |
| WO | 2006051023 | 5/2006 |
| WO | 2009/073037 | 6/2009 |

OTHER PUBLICATIONS

International Preliminary Report on Patentability, dated Sep. 10, 2010 (12 pages).
Response to Report on Patentability, dated Sep. 16, 2010 (1 page).
Corrected Version of International Preliminary report on Patentability, dated Sep. 27, 2010 (12 pages).
European Search Report for Application No. 10188676.0, dated Feb. 17, 2011 (8 pages).
International Search Report for Application No. PCT/EP2005/054804, dated Dec. 12, 2005 (2 pages).
International Search Report for Application No. PCT/SE93/00690, dated Dec. 23, 1993 (2 pages).
Office Action from the Japanese Patent Office for Application No. 2011-514529 dated Sep. 11, 2012 (4 pages).
Office Action from the United States Patent and Trademark Office for U.S. Appl. No. 12/937,906 dated Mar. 18, 2013 (6 pages).

* cited by examiner

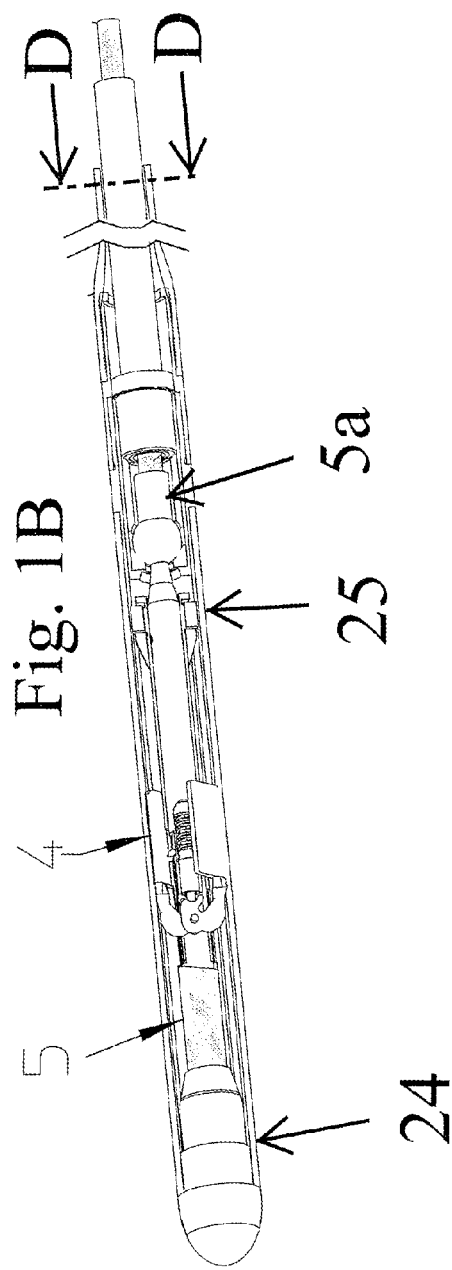
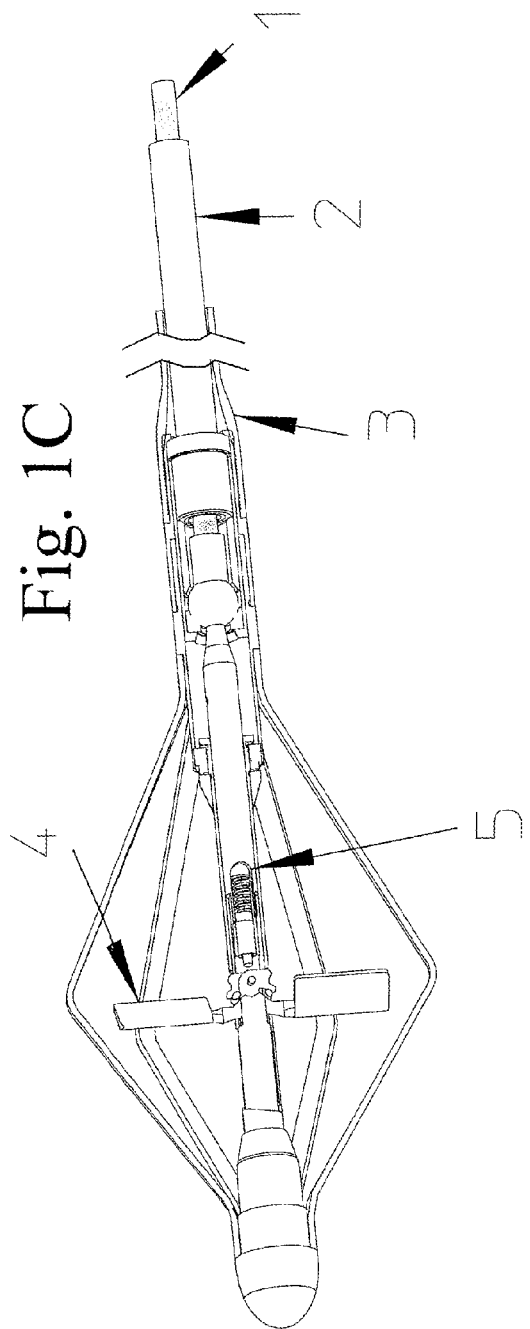

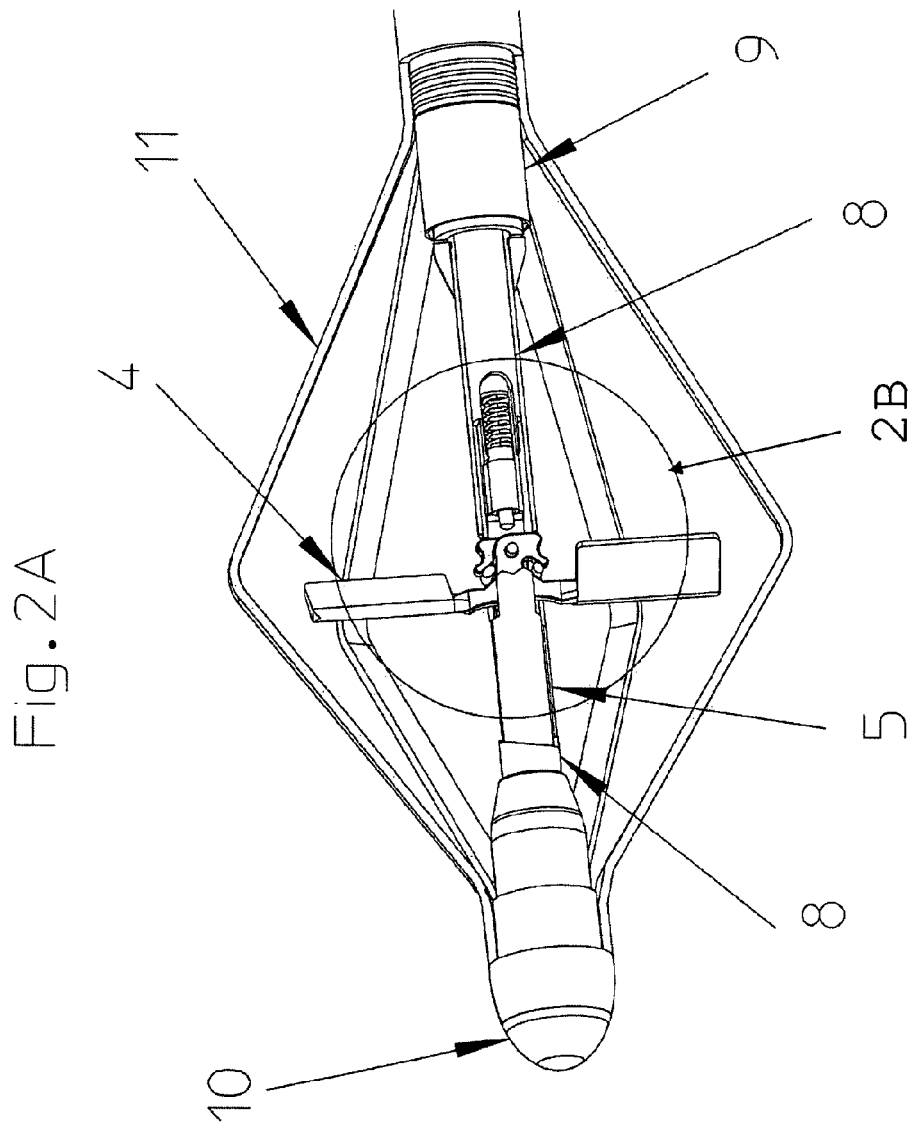

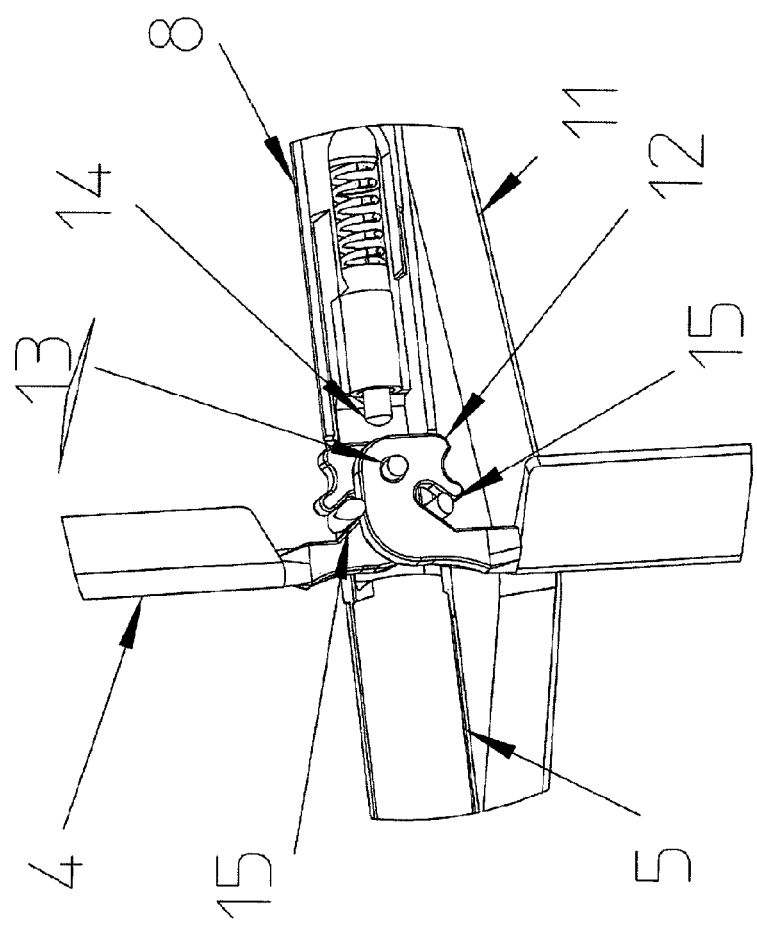

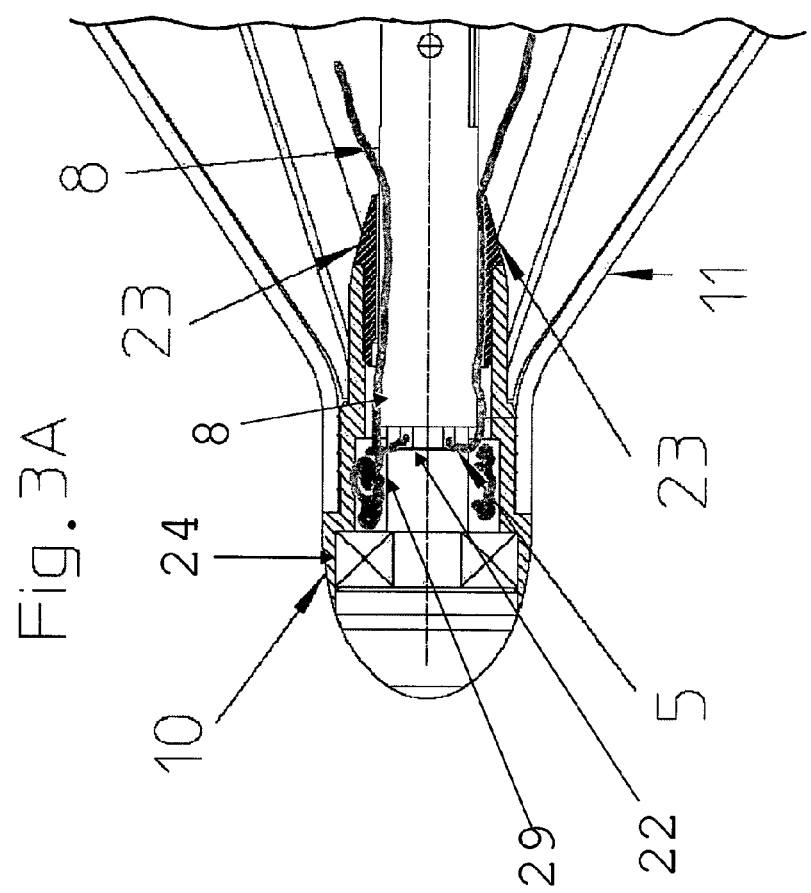

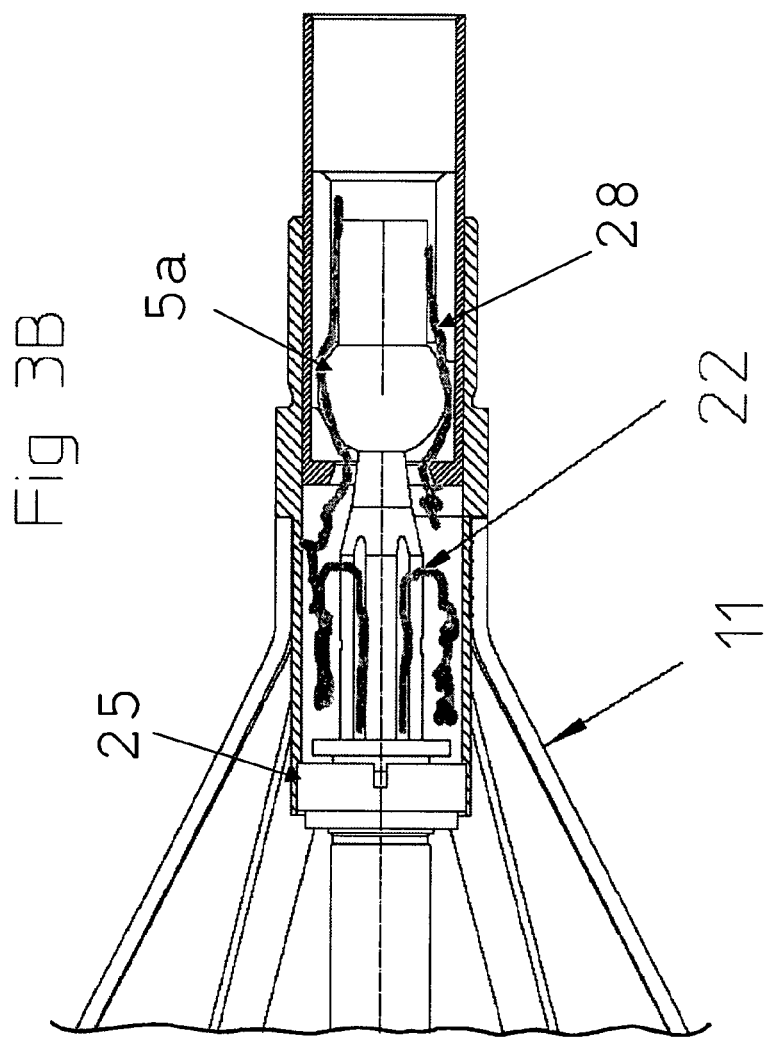

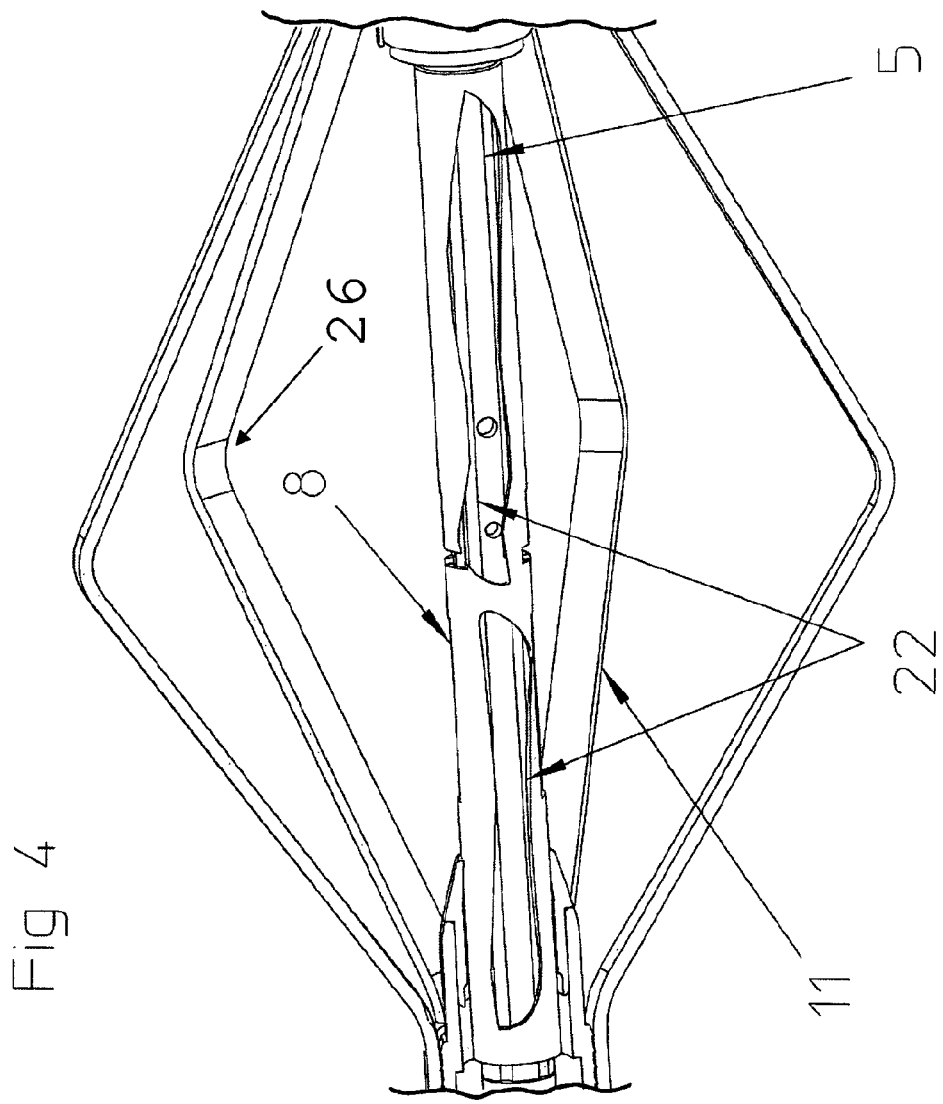

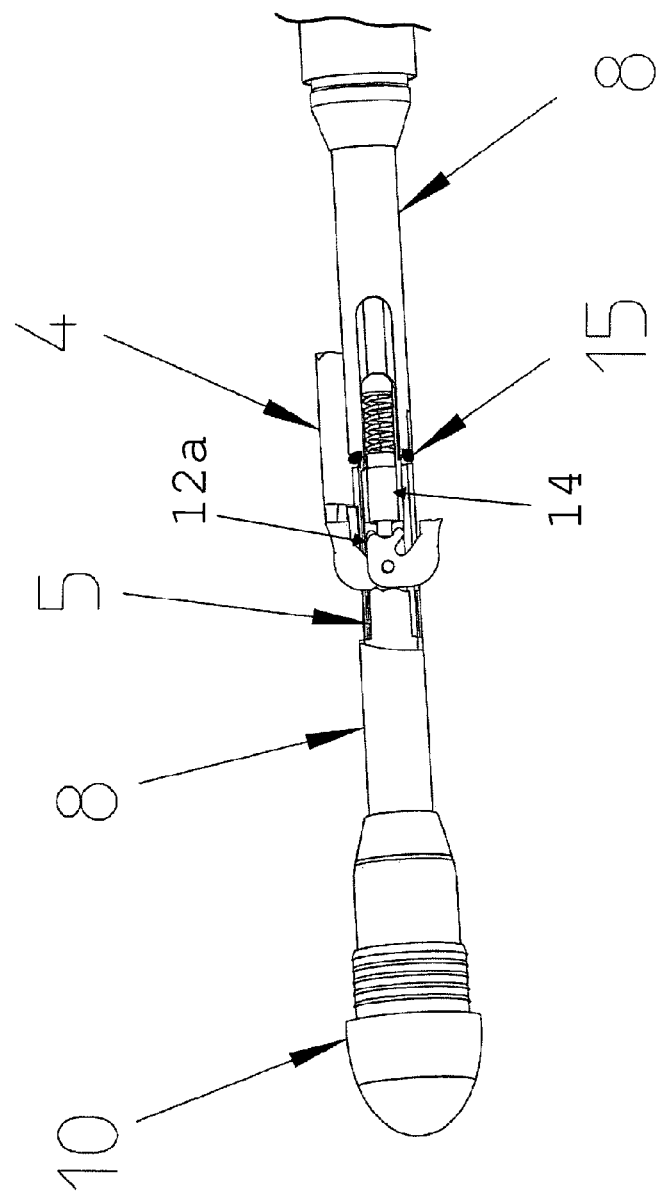

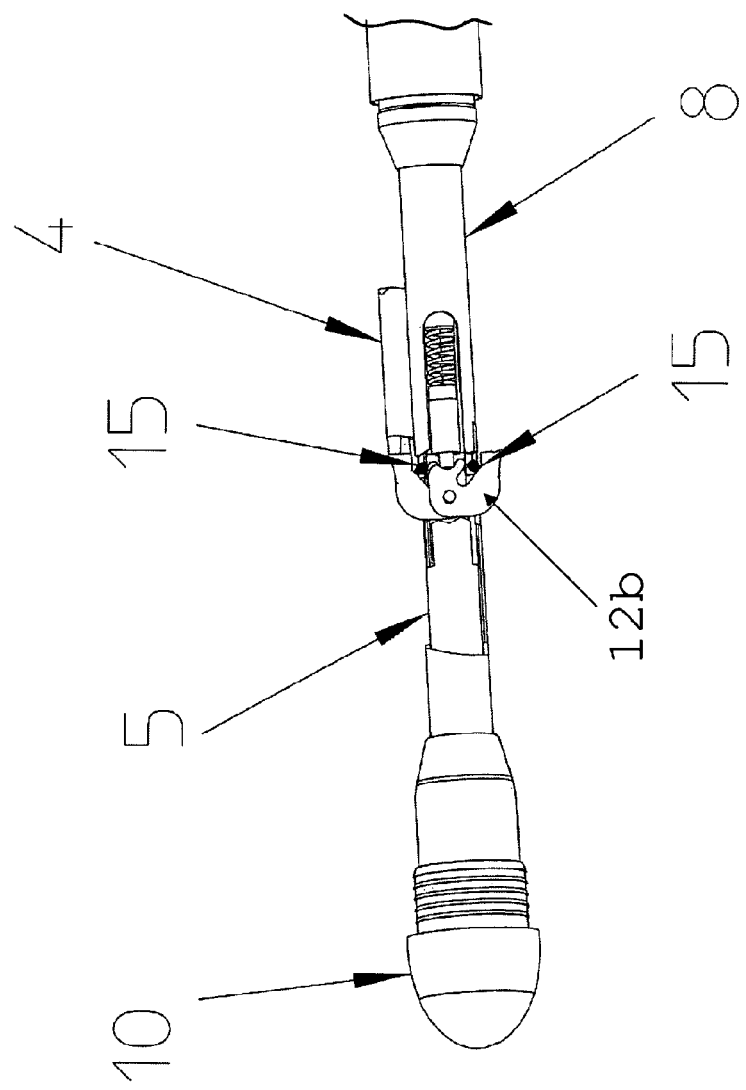

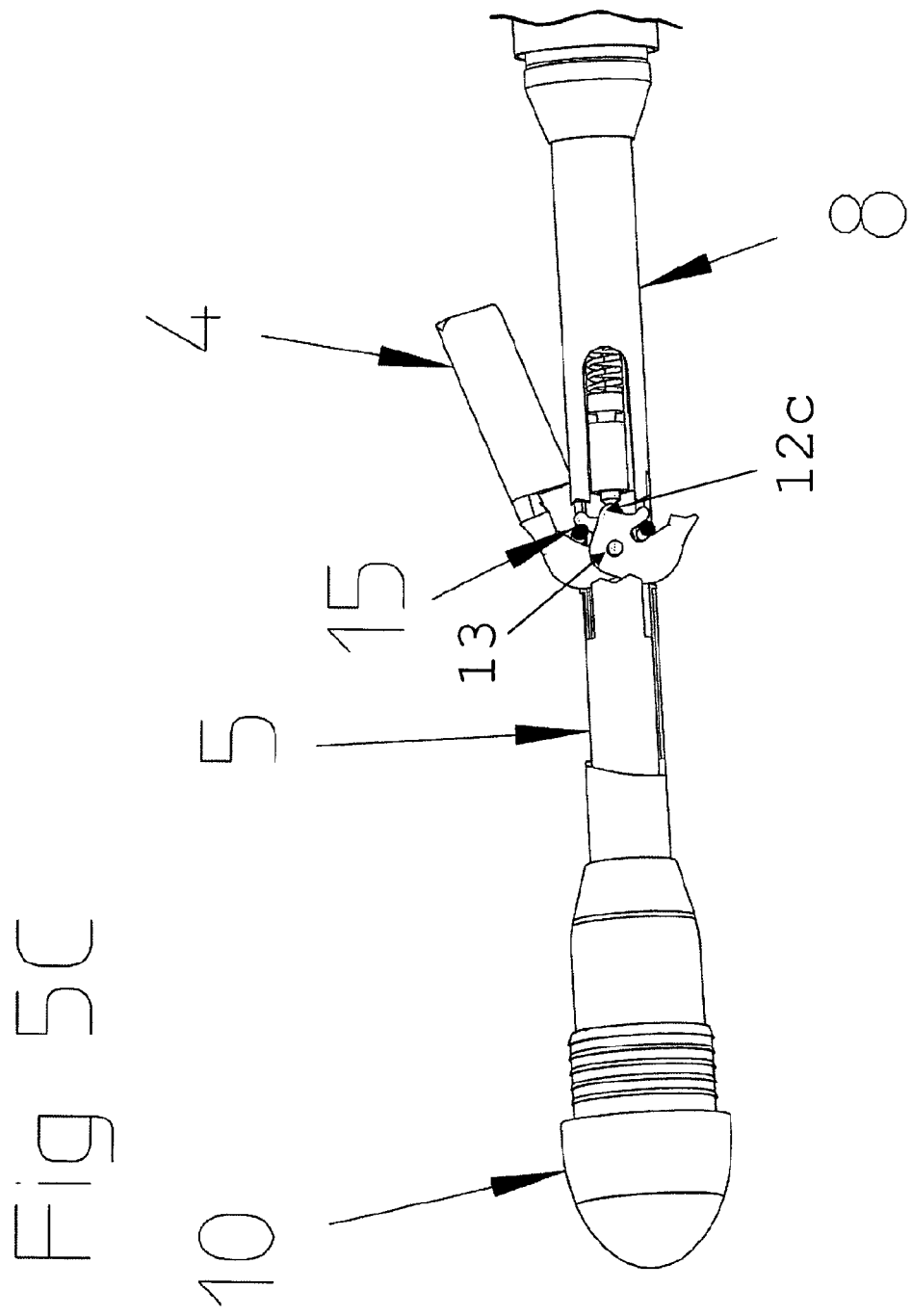

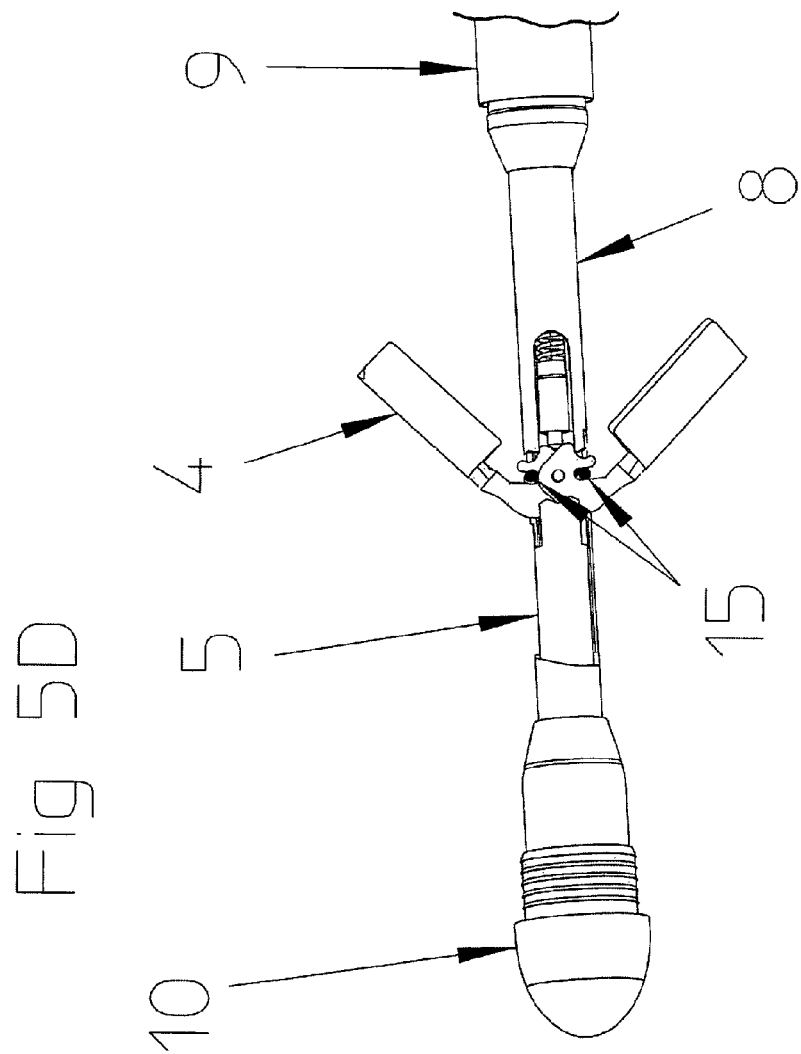

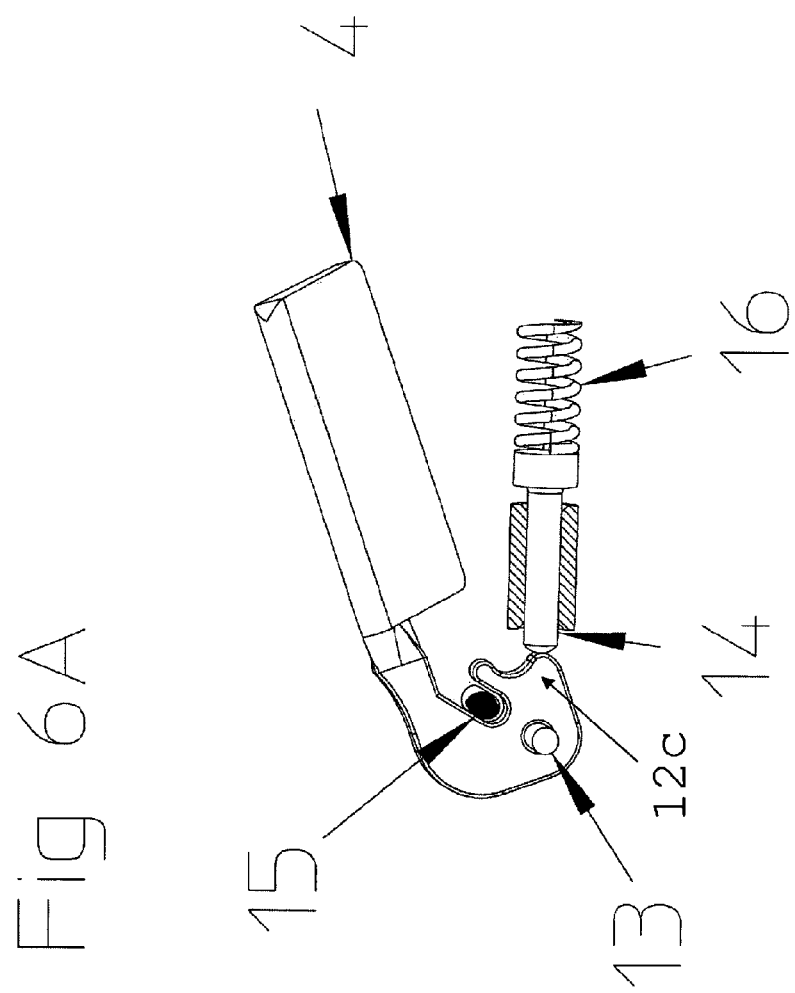

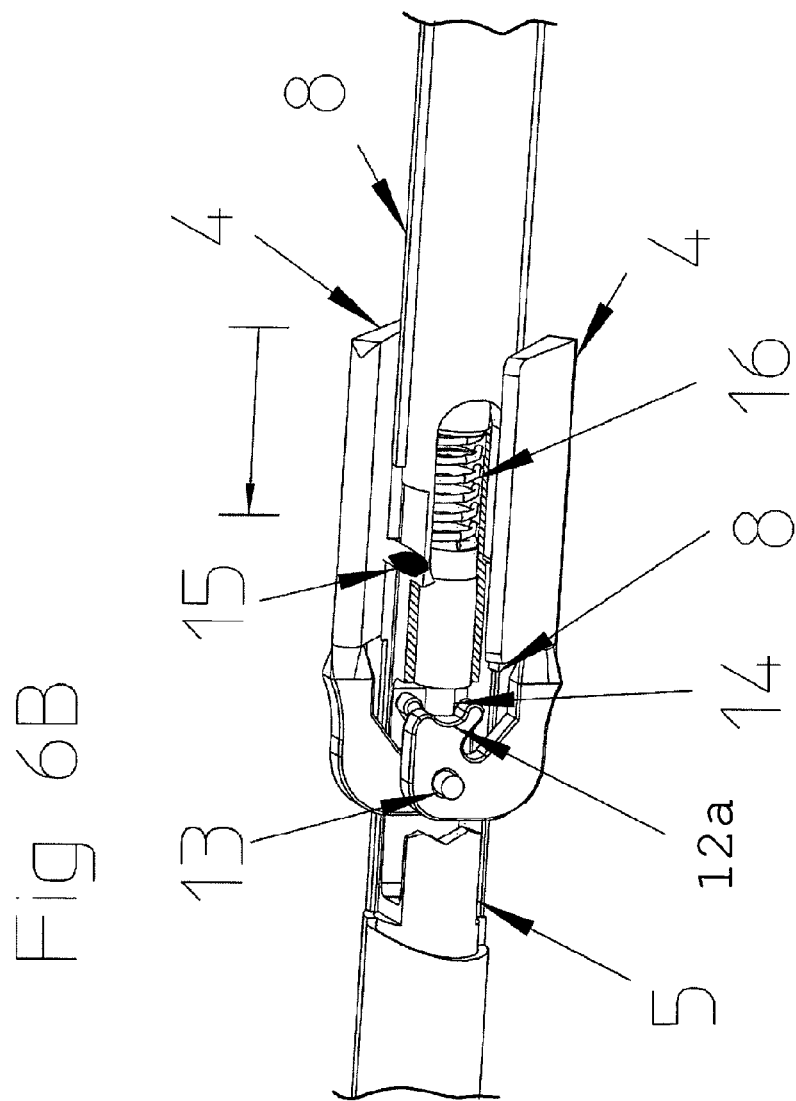

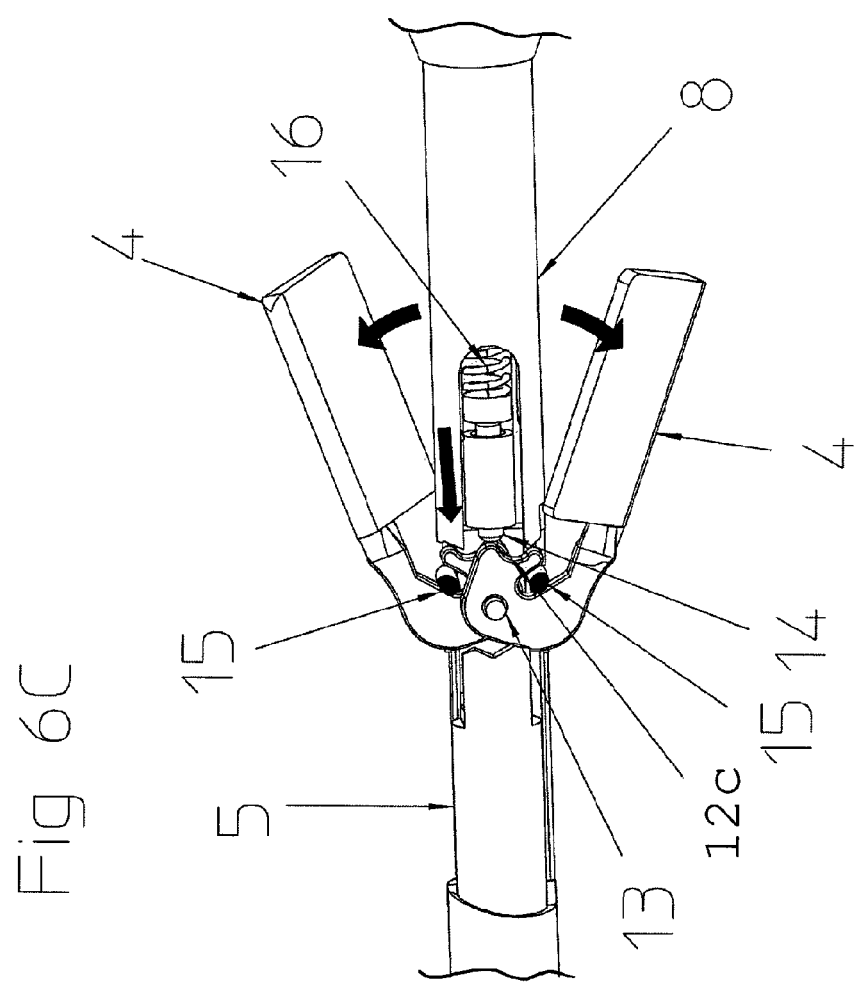

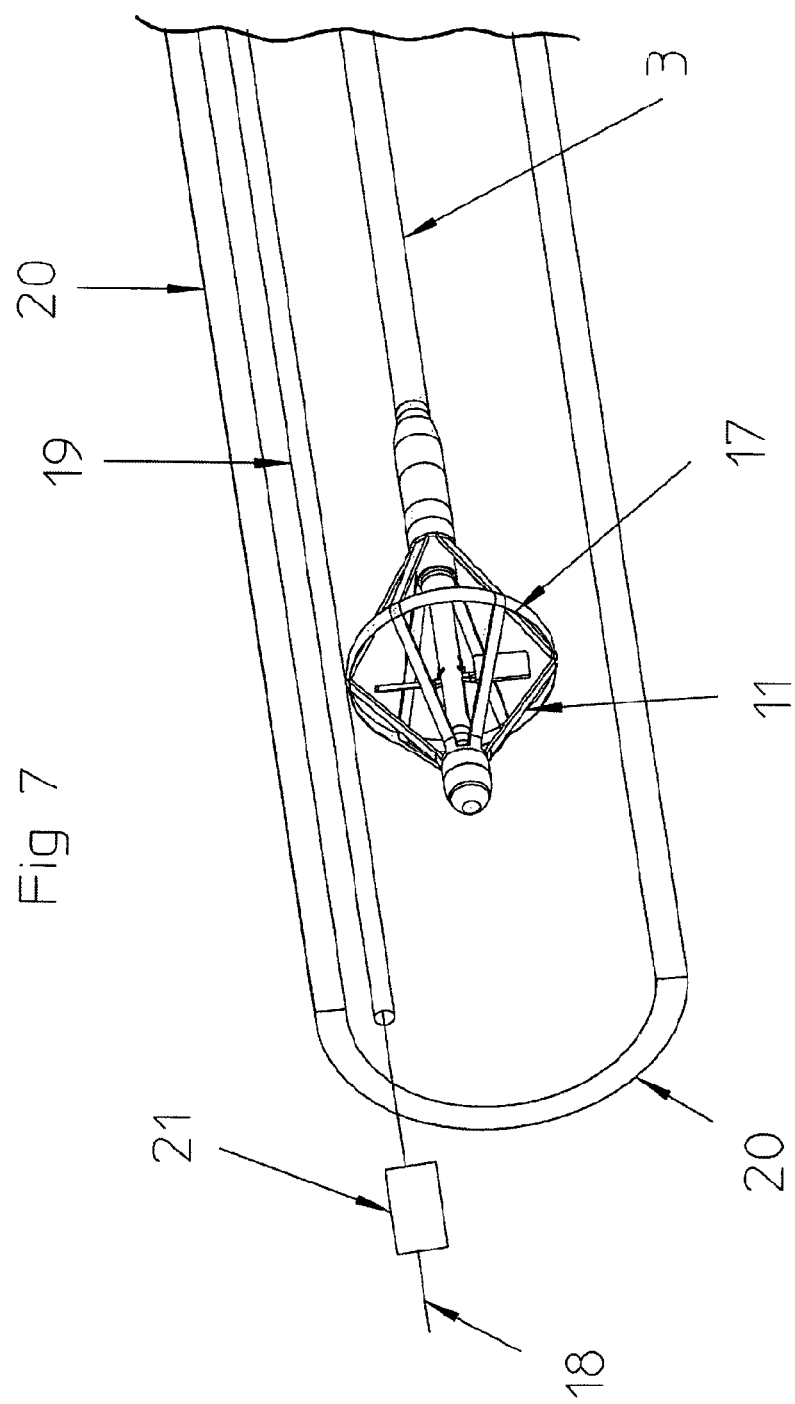

CATHETER PUMP FOR CIRCULATORY SUPPORT

CROSS-REFERENCE TO RELATED APPLICATIONS

This patent application is a divisional application of U.S. patent application Ser. No. 12/937,906, filed Oct. 14, 2010, is now U.S. Pat. No. 8,579,858, which is a national stage filing under 35 U.S.C. 371 of International Application No. PCT/SE2009/000318, filed 22 Jun. 2009, which claims foreign priority to Swedish Patent Application No. 0801459-9, filed 23 Jun. 2008, and Swedish Patent Application No. 0801460-7, filed 23 Jun. 2008, the disclosures of which are incorporated by reference herein in their entireties. Priority to each application is hereby claimed.

AREA OF INVENTION

The invention relates to a catheter pump intended to be introduced into the body of a mammal, for example via the femoral artery and placed in for example the aorta for circulatory support of the heart. The catheter pump may be arranged after the left ventricular valve in the aorta or after the right ventricular valve in the pulmonary artery.

BACKGROUND OF INVENTION

A previous device for circulatory support is known from U.S. Pat. No. 5,749,855, having the same inventor as the present invention. The device comprises a drive cable, with one end of the drive cable being connectable to a drive source and a collapsible drive propeller at the other end of the drive cable. The collapsible drive propeller is adjustable between a closed configuration in which the collapsible drive propeller is collapsed on the drive cable and an open configuration in which the collapsible drive propeller is expanded so as to be operative as an impeller. A sleeve extends between one side of the collapsible drive propeller and the other side of the collapsible drive propeller with the sleeve being movable between configurations in which the collapsible drive propeller is in the open and closed configuration. A lattice cage is arranged surrounding the propeller and is folded out at the same time as the propeller.

This device operates very well in many circumstances. However, there is still room for improvements. For example, it would be safer if the lattice cage is folded out before the propeller is folded out. In addition, the shaft supporting the propeller needs to be journalled with bearings, and such bearings need to be lubricated.

Other catheter pumps are known from US 2008/0132748 A1, US 2008/0114339 A1 or WO03/103745A2.

SUMMARY OF THE INVENTION

Accordingly, an object of the present invention is to mitigate, alleviate or eliminate one or more of the above-identified deficiencies and disadvantages singly or in any combination.

According to an aspect of the invention, there is provided a catheter pump according to claim 1.

A spring-loaded bolt may be arranged for cooperation with cam surfaces of said propeller. In an embodiment, there may be arranged a purge fluid system comprising an axial lumen in said hollow catheter for providing fluid to a proximal bearing at the proximal side of the drive shaft; channels in said drive shaft for providing fluid to a distal bearing at the distal side of the drive shaft; and a lip seal for passing the fluid from the distal bearing and out to the surroundings.

BRIEF DESCRIPTION OF THE DRAWINGS

Further objects, features and advantages of the invention will become apparent from the following detailed description of embodiments of the invention with reference to the drawings, in which:

FIGS. 1B and 1C are cross-sectional views showing the pump head according to an embodiment of the invention. FIG. 1B shows the folded pump head during insertion and FIG. 1C shows the pump head in an unfolded or deployed position.

FIG. 2A is a perspective view, partly broken, and shows the deployed distal part of the catheter pump head.

FIG. 2B is a magnified view of the central part of FIG. 2A encircled by the circle 2B.

FIGS. 3A and 3B are cross-sectional views showing the housing of and the tip and body bearings of the propeller shaft.

FIG. 4 is a partially broken perspective view showing the propeller shaft with parts of the sliding outer sleeve removed for illustrating longitudinal channels on the outer surface of the propeller shaft.

FIGS. 5A to 5D are perspective views showing how the propeller blades are deployed from the folded position to the unfolded position.

FIGS. 6A to 6C are partial views showing the unfolding mechanism in an enlarged scale of the propeller shown in FIGS. 5A to 5D.

FIGS. 7 to 11 are perspective and end views showing how the catheter pump can be used in combination with other treatment devices and/or diagnostic tools.

DETAILED DESCRIPTION OF EMBODIMENTS

Figure 1A:
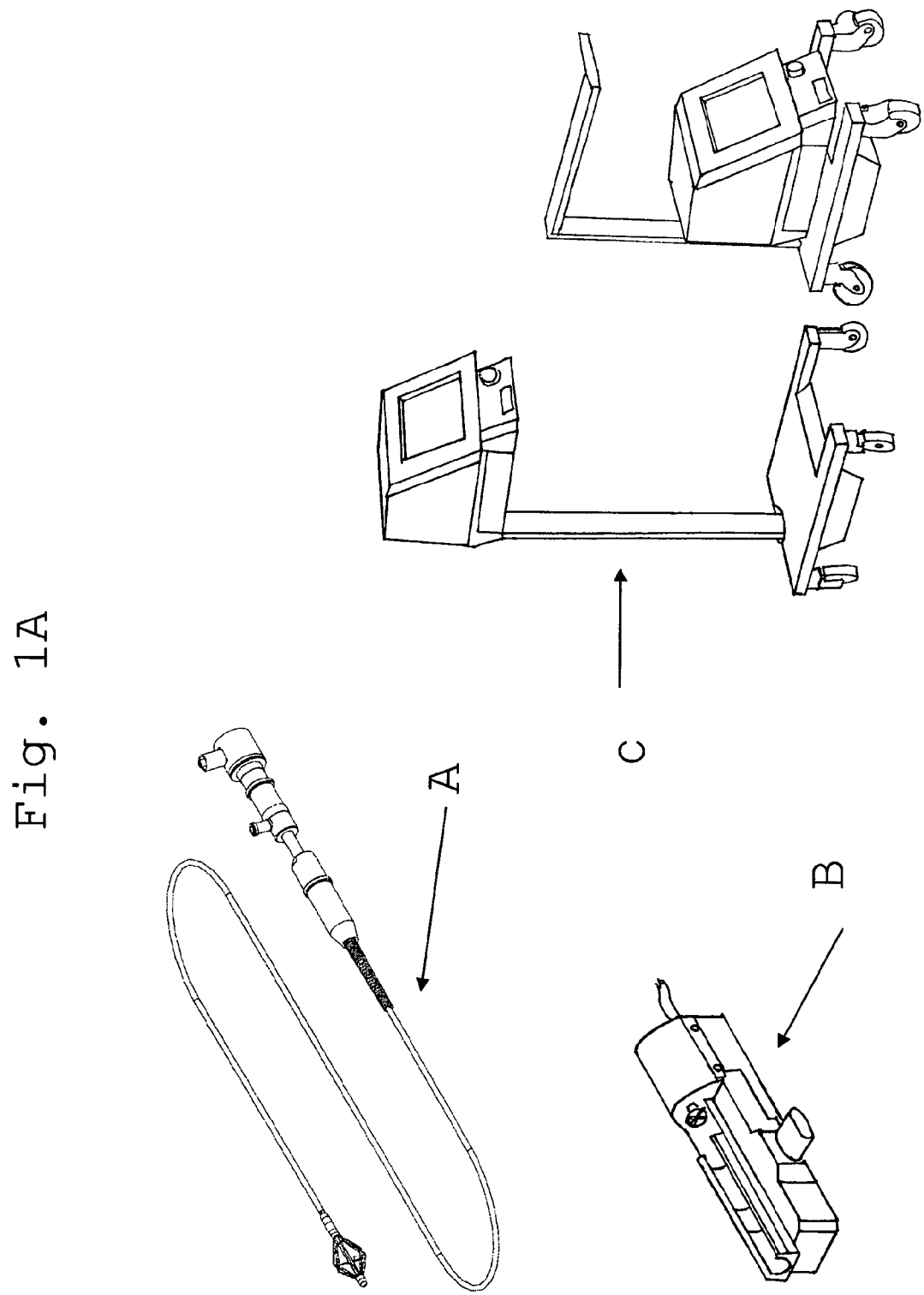
FIG. 1A is a schematic view in perspective of a system according to an embodiment of the invention.

Below, several embodiments of the invention will be described with references to the drawings. These embodiments are described in illustrating purpose in order to enable a skilled person to carry out the invention and to disclose the best mode. However, such embodiments do not limit the invention. Moreover, other combinations of the different features are possible within the scope of the invention.

"The Reitan Catheter Pump System" is a temporary circulatory support system based on the concept of a foldable propeller at the tip of a flexible catheter according to an embodiment. The system is used in patients with heart failure when the native heart is unable to support the body with sufficient oxygenated blood. The basic principles of the system corresponds to that described in U.S. Pat. No. 5,749,855 mentioned above.

There are several blood pumps on the market, but most of them require major surgery to be implanted. The use of a foldable propeller has therefore the advantage that while folded during the insertion it makes it possible to introduce a large dual-winged propeller with high-flow capacity into the body without the need of surgery. The propeller is arranged at the distal end of the catheter in the pump head. In addition to the propeller, the pump head also comprises a cage made of six filaments surrounding the propeller in order to protect the aorta against the propeller.

The insertion is accomplished percutaneously via a puncture in the femoral artery in the groin through an introducer sheath and the pump is advanced into the thoracic aorta with the pump head placed approximately 5 to 10 centimeters below the left subclavian artery.

Once in position, the propeller and its protective cage are deployed or unfolded. The pump is then ready for operation. The rotation of the propeller creates a pressure gradient inside the aorta. The blood pressure decrease created in the upper part of the aorta facilitates the ejection of blood from the left ventricle. The increased pressure in the lower part of the aorta facilitates the perfusion of the internal organs, especially the kidneys.

The pump is mounted on a flexible catheter with an inner rotating wire which is connected to a DC motor at the proximal end. The motor is operated with adjustable rotational speed, monitored by a specially designed console.

The pump has a purge system with two small channels, which transport a 20% glucose solution to the proximal bearing of the propeller shaft for lubrication and purging. Two thirds of this fluid enters the patient's circulation, and one third of the fluid is returned to a waste bag. The return fluid passes along the drive wire, which receives lubrication.

The advantage of making the system foldable is to be able to introduce a large propeller into the body without any large surgery. The size of the folded pump head and the flexible catheter is approximately 10 French (3.3 mm) in diameter. The system comprises four main components:
1. The catheter pump head,
2. The drive unit,
3. The console,
4. The purge set.

The catheter has been designed such that it will be advanced through the femoral artery into the aorta, so that the pump resides 5 to 10 cm below the subclavian artery in the descending aorta. The catheter pump head comprises a flexible outer catheter or sheath and an inner, hollow catheter, which slide against one another to deploy the protective cage and unfold the propeller within the cage. There is a flexible drive wire running through the central lumen of the inner catheter. The inner catheter also has two small channels for transporting 20% glucose solution to the pump head for lubrication and purging. One-third of the fluid is returned via the internal drive shaft lumen, and two-thirds of the fluid is added to the blood pool.

The pump head is mounted at the distal end of the flexible catheter. Filaments surrounding the propeller are foldable, forming a protective cage around the propeller when the propeller/cage system is unfolded. The folded pump head during insertion measures 3.3 mm (10 French), whereas the deployed pump head measures approximately 19.5 mm. The rotation of the propeller is transmitted via the flexible drive wire placed in the central lumen of the inner catheter.

The proximal end of the catheter (the drive coupling) is connected via a magnetic field to a DC motor, which is placed in a Drive Unit. The speed of the DC motor, rotating wire and propeller is adjustable and is monitored by a console. The speed can be adjusted between 1,000 and 15,000 rpm.

The drive unit has been designed such that it may be positioned at the bedside of the patient and has a magnetic coupling for connection to the catheter pump at one end. The other end of the drive unit is connected to the console via an electric cable.

The primary functions of the console are to monitor and control the speed of the catheter pump and a peristaltic pump for the purge fluid. All controls and monitoring parameters for the system are displayed on a touch screen. The console also comprises battery or electric power for the Drive Unit. The purge system is constructed to lubricate and to prevent entrance of blood into the rotating parts of the pump. The rotation of the propeller is transmitted from the external DC motor via magnetic coupling and a flexible wire in the center of the catheter.

The purge system consists of small channels inside the catheter to transport a 20% sterile glucose solution to lubricate the internal components. Heparin may be added to the purge fluid. One-third of the fluid is transported back through the inner lumen and lubricates the rotating wire. Two-thirds of the glucose solution enters the circulation of the patient and seals off the drive shaft. The total amount of purge fluid may be set to 600 ml per 24 hours (about 0.4 ml per minute) and is transported via a peristaltic pump. The console controls the speed of the peristaltic pump. FIG. 1 discloses an overview of a system according to an embodiment. The system comprises a catheter A intended to be introduced into the body of a mammal, such as a human, via the femoral artery and placed in the aorta for circulatory support of the heart. The catheter is relatively long so that it can extend from the percutaneous introduction site into for example the femoral artery in the groin and up to the aortic arc.

The catheter comprises a pump head with a propeller enclosed within a cage as described in more details below. The pump head may be placed in the intra-aortic balloon position in the thoracic aorta. Other positions may be used as well.

The other end of the catheter extends at the proximal end out of the mammal and is connected to a drive unit B, which also will be further described below. The drive unit B is connected to and controlled by a control console C, which may comprise batteries, touchscreen displays and a computer system. The distal portion of the catheter, i.e. the pump head, is shown in FIGS. 1B and 1C.

The catheter comprises a drive wire 1 which is flexible and can transmit torque although it can be bent to some extent. The drive wire 1 is enclosed in an inner, hollow catheter 2, which in turn is enclosed in an outer catheter or sheath 3.

In the present specification, the expression "distal" has the meaning of facing away from the percutaneous introduction site and "proximal" has the meaning of being closer to the percutaneous introduction site than the "distal".

The drive wire 1, the hollow catheter 2 and the sheath 3 extend along the entire catheter pump, as shown by the cut lines in FIGS. 1B and 1C.

The drive wire 1 is at its distal end connected to a drive shaft 5. A foldable propeller 4 is attached to the shaft in a folded position shown in FIG. 1B.

Figure 1D:
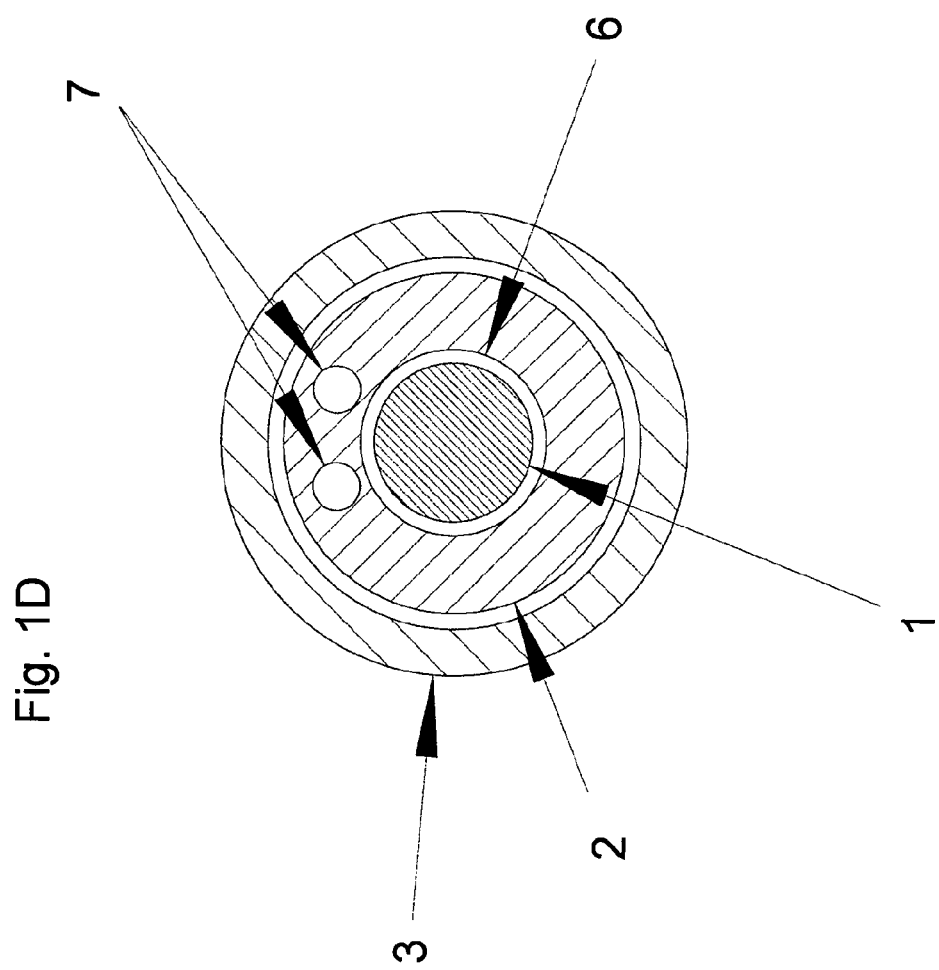
FIG. 1D is a cross-sectional view taken line D-D in FIG. 1B.

As shown in the cross-sectional view of FIG. 1D, the inner catheter 2 comprises a cylinder having a central lumen 6, in which the drive wire 1 is arranged. In addition, the inner catheter 2 comprises two axial holes 7, as will be further described below. The inner catheter is relatively rigid in the longitudinal direction and is flexible in the cross-direction. Thus, the catheter has a sufficient rigidity to be inserted into the vascular system and moved to a desired position by itself. The catheter has also a sufficient flexibility to follow the curvature of the vascular system.

If a guide wire is used for inserting the catheter pump, the guide wire may extend inside one of the holes 7.

Figure 3C:
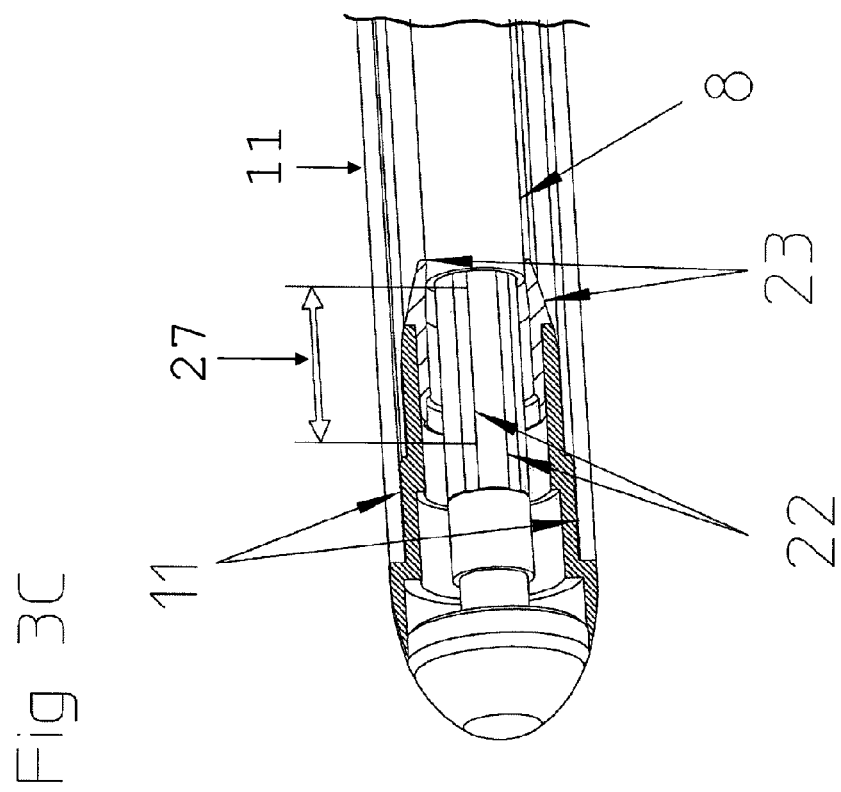
FIG. 3C is a partially broken view of a portion of FIG. 3A.

The drive wire 1 fits into the central lumen 6 with a small clearance as shown in FIG. 1D. The clearance may comprise a lubricant so that the drive wire 1 may rotate freely in the catheter 2, which is non-rotating. The sheath 3 surrounds the inner catheter 2 with a clearance. The sheath 3 is moveable in the axial direction in relation to the inner catheter 2 as will be described below. In the pump head, the distal end of the drive wire 1 is attached to a nipple 5 a arranged at the proximal end of the drive shaft as shown in FIG. 1B. The drive shaft is journalled in distal bearings 24 and proximal bearings 25 as shown in FIGS. 1B, 3A and 3B. A proximal housing 9 and a distal housing 10 are arranged adjacent the distal and proximal ends of the drive shaft 5. Several filaments 11 are arranged between the housing 9 and the housing 10. In the folded position, the filaments 11 are parallel with the drive shaft 5 and extend close to the drive shaft as shown in FIGS. 1B and 3C. The drive shaft 5 is covered by a sleeve 8, which is moveable in the axial direction on the drive shaft 5. In the folded position, the sleeve 8 extends from the proximal housing 9 and ends a short distance 27 before the distal housing as shown in FIG. 3C.

The distal housing 10 is attached to the inner catheter 2 and the drive wire 1 via the drive shaft 5. The proximal housing 9 is attached to the outer catheter or sheath 3 as appears from FIG. 2A. The outer catheter 3 is moveable in the axial direction in relation to the inner catheter 2. When the outer catheter 3 is moved in the direction downward in FIG. 2A, the proximal housing 9 is advanced towards the distal housing 10 resulting in the fact that the filaments 11 are bent outward in order to form a cage, as shown in FIG. 2A. Such bending of the filaments 11 may be facilitated by weakening lines 26, see FIG. 4, arranged at the inside of the filaments 11, close to the middle thereof.

When the cage has been initially formed, continued movement of the outer catheter 3 and the proximal housing 9 towards the distal housing 10 results in that the folded propeller is unfolded to the position shown in FIG. 2A, as further described below in connection with FIGS. 5A to 5D. The cage thus formed, protects the inner walls of a blood vessel 20 from the propeller. Since the cage is unfolded before the propeller is unfolded and by the same movement as the unfolding of the propeller, it is assured that the cage is formed before the propeller is unfolded. Thus, the blood vessels are protected from the propeller also during the unfolding of the propeller, which is an advantage. As shown in FIG. 2B, the propeller 4 comprises two blades 4 which are journalled by a propeller pin 13 extending through the drive shaft 5. Moreover, each propeller blade comprises a cam surface 12 for cooperation with a spring bolt 14 and an actuation pin 15 attached to the sleeve 8.

The complete movement of the outer catheter 3 and the proximal housing 9 towards the distal housing 10 corresponds to the short distance 27 shown in FIG. 3 C and mentioned above.

As shown in FIG. 3B, the outer surface of the drive shaft is provided with several channels 22 extending along the entire drive shaft inside the sleeve 8.

A lubricant and purge fluid is introduced into one or both of the holes 7, see FIG. 1D, at the end of the inner catheter 2 extending out of the body at the percutaneous site. The fluid exits the hole 7 adjacent the nipple 5a, as shown in FIG. 3B. The fluid, shown by line 28, encircles the nipple 5a and lubricates the proximal bearing 25 and passes out to the blood outside the bearing in order to purge the bearing and prevent blood from entering the bearing in the opposite direction.

In addition, the fluid enters the channels 22 and passes towards the distal housing. Moreover, a portion of the fluid is diverted into the clearance between the inner catheter 2 and the flexible drive wire 1 inside the central lumen 6, as shown in FIG. 1D. This fluid will lubricate the drive wire and ensure that the drive wire will operate smoothly. This fluid will return to the percutaneous site and be collected. The portion of the fluid returning this way is approximately one third of the total flow.

The fluid entering the channels 22 at the proximal housing 9 will exit the channels 22 at the distal housing 10 as indicated by line 29 in FIG. 3A. The fluid will encircle the distal bearing 24 and lubricate the bearing. The fluid will pass outside the sleeve 8 and beyond a lip seal 23 arranged surrounding the sleeve 8. The sleeve 8 is moveable in relation to the lip seal 23 between the position shown in FIG. 3C, when the filaments and the propeller are folded, and the position shown in FIG. 3A, when the propeller and the cage are unfolded. The fluid finally enters inside the blood vessel via the lip seal 23 and prevents blood from passing in the opposite direction.

Thus, by this arrangement, both the proximal bearing 25 and the distal bearing 24 are lubricated by the fluid and the fluid purges the inside of the proximal housing 9 and the distal housing 10 so that no blood can enter inside the housings. As shown in FIG. 3C, the channels 22 are open to the interior of the distal housing also in the folded position of the cage and propeller. Thus, purge fluid can be provided before unfolding the cage and propeller and before starting any propelling action, which is an advantage.

Alternatively or additionally, the channels 22 can be placed on the inner surface of the outer sliding sleeve 8 or arranged as axial holes in the center of the drive shaft. Both the drive shaft 5 and the sleeve 8 are rotating in common.

With reference now to FIGS. 5A to 5D, the unfolding of the propeller will be described. The unfolded cage with the filaments 11 is not shown so that the other details will be clearly visible. As appears from FIGS. 5A and 6B, in the folded position of the propeller blades 4, a spring bolt 14 engages a cam surface 12a of the propeller blade and keeps the propeller blade in the folded position. The spring bolt 14 is biased by a spring 16, see FIG. 6B.

Two actuation pins 15 are arranged at the sleeve 8. When the sleeve 8 is advanced in the downward direction in order to unfold the cage, the actuation pins 15 are moved to the position shown in FIGS. 5B, acting upon a second cam surface 12b of the propeller blade.

Further movement of the sleeve 8 downward will move the cam surface 12b downward, thereby pivoting the propeller blade around the propeller pin 13, as shown in FIGS. 5C and 6A. This action is counteracted by the spring bolt 14. The spring bolt is forced to pass over a cam shoulder 12c as shown in FIGS. 5C, 5D and 6A.

Further movement of the sleeve 8 downward will unfold the propeller to the position shown in FIG. 2B. The opposite actuation pin 15 prevents the propeller blade 4 from moving over the 90 degree position.

When the propeller is fully unfolded, the spring bolt 14 has lost its contact with the cam surface of the propeller blade, as appears from FIG. 2B. In this position, the propeller blade is locked by the actuation pin 15.

The propeller blade will be retracted to the folded position at the opposite movement of the actuation pin 15. Then, the cage will be collapsed to the folded position.

Thus, it appears that the cage is unfolded or deployed before the propeller is unfolded. The propeller is unfolded in a partly or completely deployed cage. This prevents the walls of the blood vessel from possible sharp edges during the unfolding of the propeller blades. FIG. 7 shows another embodiment of the catheter pump, wherein the cage is provided with a girdle 17 surrounding the filaments at the outer positions thereof. This arrangement enables the addition of a guide wire 18, which may pass the catheter pump without influencing upon the operation or the pump or contacting the propeller blades during rotation thereof.

Alternatively or additionally, a guide tube 19 may be inserted in a blood vessel 20 and passing the pump head. A treatment device 21 can be inserted by means of the guide wire 18 and/or the guide tube 19. The treatment device 21 may be a coronary vessel dilation and stenting device, an ultrasound coronary artery device, a drug delivery device, a left ventricular pressure measurement device, a conductance catheter for pressure volume loops, a catheter for electrophysiology of the left ventricle, a micro camera, a video camera, a balloon catheter, coronary angioplasty catheter, etc.

Figure 8:
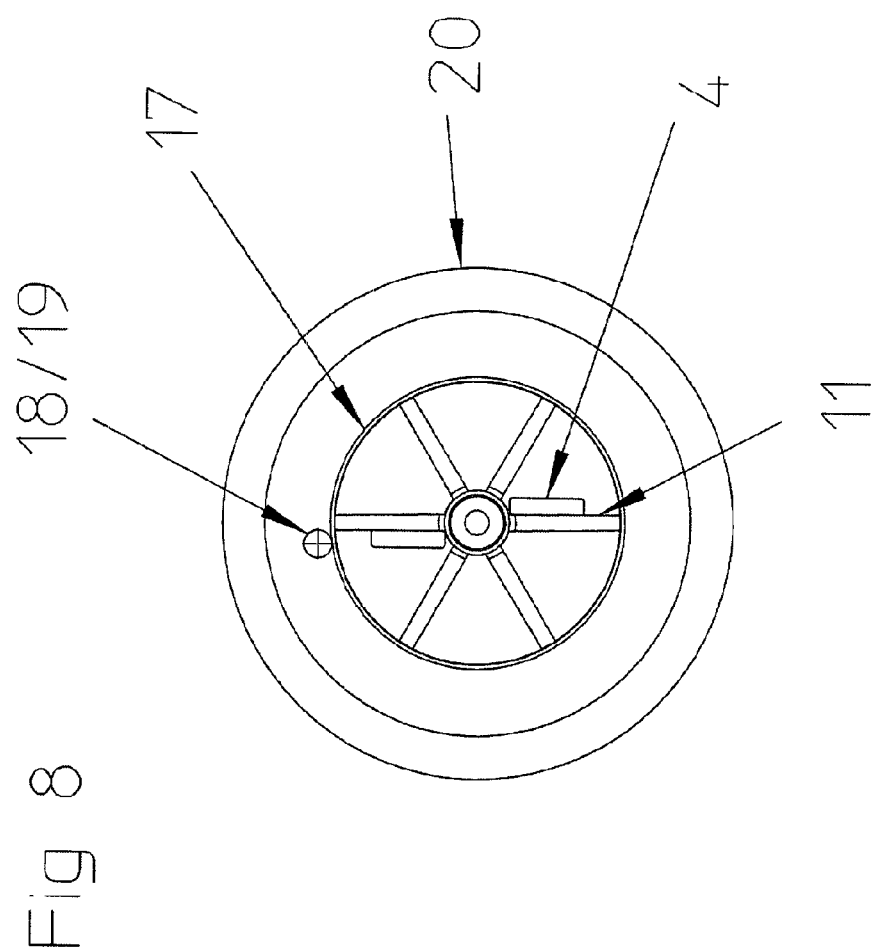
Figure 9:
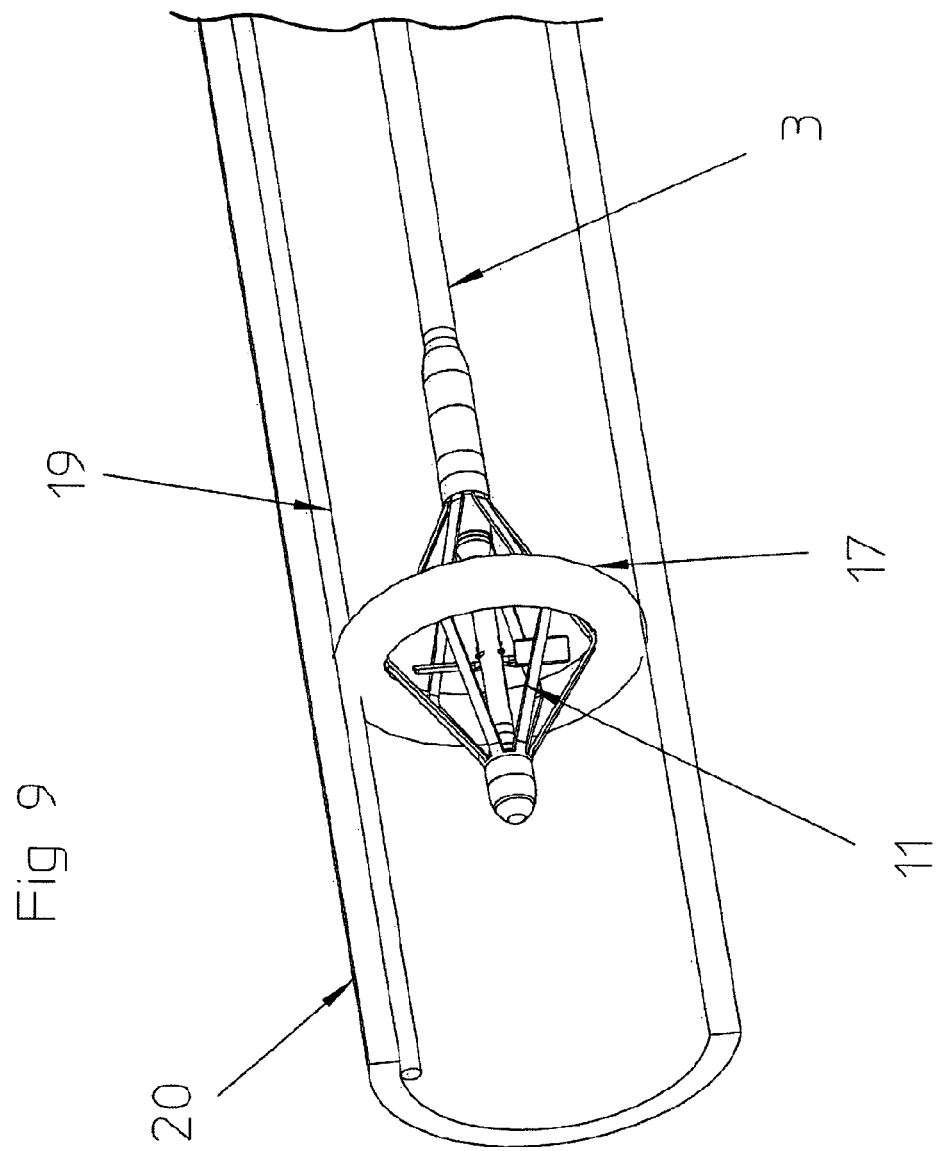
Figure 10:
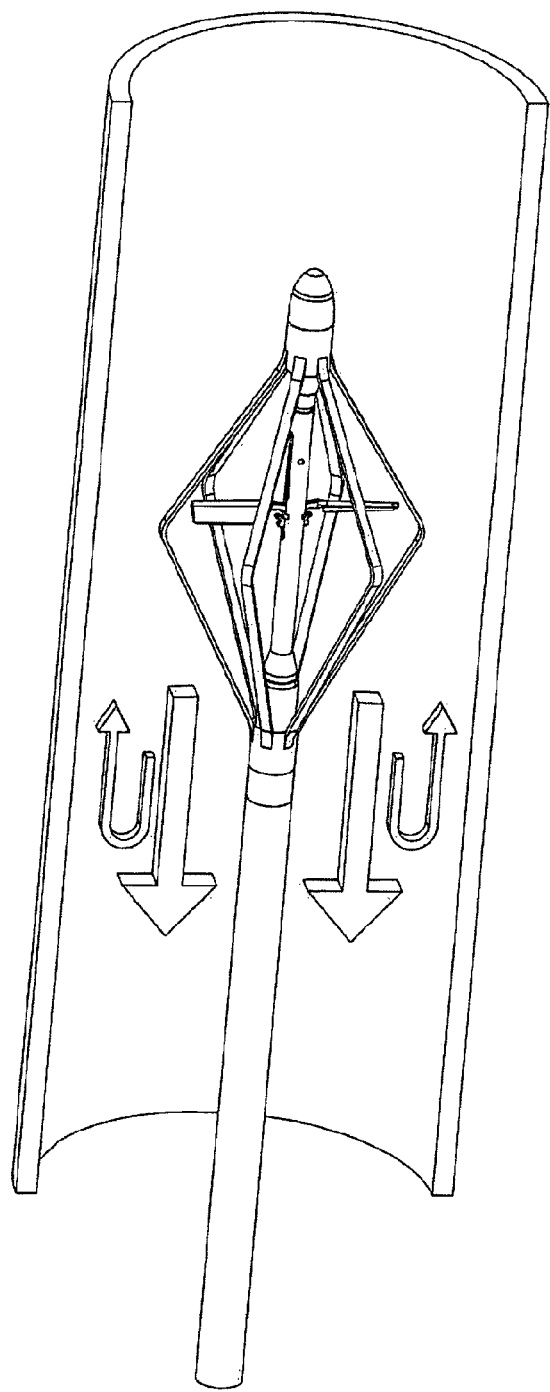
Figure 11:
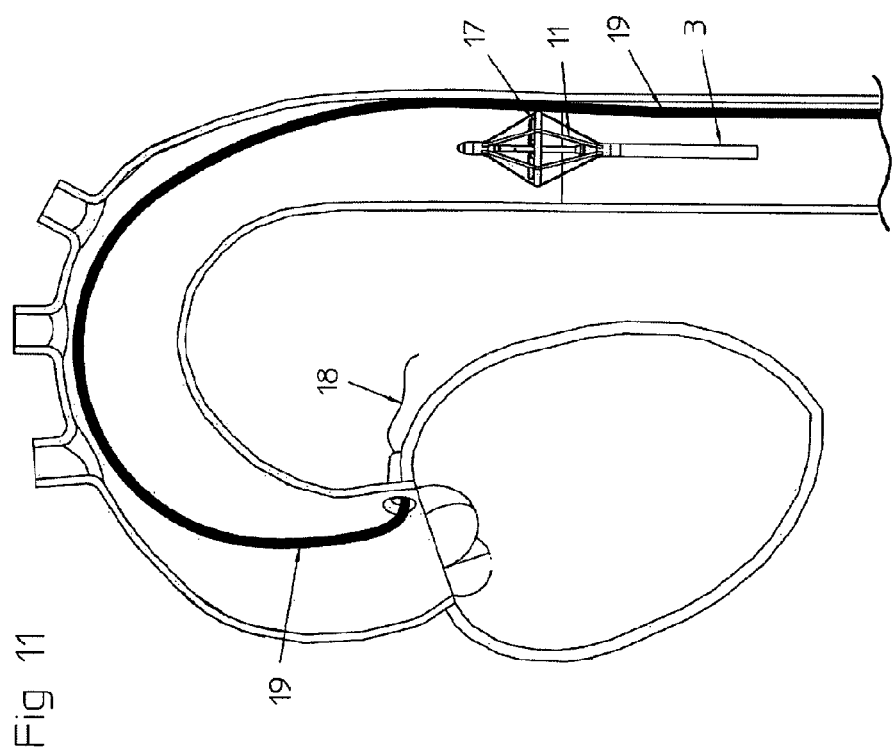

FIG. 8 is an end view showing the arrangement according to FIG. 7. As shown in FIG. 9, the girdle 17 may be arranged as an inflatable ring. In this manner, back-flow of blood may be reduces along the wall of the vessel 20. The flow pattern of the back flow without such a ring is further illustrated in FIG. 10. FIG. 11 shows a catheter pump inserted into the aorta in a position near the heart. The guide tube 19 extends outside the catheter pump. The guide tube 19 is inserted with help of the guide wire 18. The insertion of at least the guide wire 18 may be accomplished before the insertion of the catheter pump and deployment of the cage 11. The girdle 17 prevents both the guide wire 18 as well as the guide tube 19 from coming in contact with the propeller 4. Outside the body, the catheter device A is connected to a drive unit B as shown in FIG. 1.

The drive unit comprises an electric motor having a radial disk arranged at its shaft. The disk comprises several permanent magnets attached to the surface of the disk. The flexible drive wire 1 ends with a similar disk provided with permanent magnets. The disks of the motor and the disk of the drive wire are brought into close distance from each other. Then, the magnets will attract and connect the two disks together. In this manner, torque from the motor can be transmitted to the drive wire. If the drive wire is prevented from rotating, for example by the fact that the propeller is blocked, the magnets of the drive disks will separate. Then, substantially no torque is transmitted from the motor, until the motor has been stopped and the magnets of the disks have been aligned and attract. This is a safety measure.

The drive unit B further comprises a peristaltic pump, which drives the purge fluid into the holes 7 in the inner catheter 2. The fact that the purge fluid is passing inside a separate channel to the proximal housing 9 and further to the distal housing 10 is an advantage. If instead the purge fluid would pass outside the drive wire, there is a risk that small particles in the drive wire may come lose and contaminate the bearings.

The purge fluid passes inside channels 22 arranged in the drive shaft 5. Thus, no separate member is required between the proximal housing and the distal housing. The purge fluid has no other way to escape from the distal housing but via the lip seal 23. The catheter pump may be arranged after the left ventricular valve in the aorta or after the right ventricular valve in the pulmonary artery. The catheter pump may be arranged adjacent the heart valves or further down the aorta or artery in any suitable position.

The catheter pump may be driven with a constant speed, which is adjusted to the needs of the patient. If required, the catheter pump may be driven with a pulsative or partially pulsative flow, for example substantially synchronously with the heart.

The catheter pump is intended for assisting the beating heart. However, the catheter pump may also be used also during heart surgery when the heart is non-beating.

Although the present invention has been described above with reference to specific embodiment, it is not intended to be limited to the specific form set forth herein. Rather, the invention is limited only by the accompanying claims and other embodiments than those specifically described above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or process. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A catheter pump intended to be inserted in the circulatory system of a mammal, the pump comprising:
   a hollow catheter having a lumen;
   a sheath surrounding said hollow catheter and being axially moveable in relation to the hollow catheter;
   a drive wire arranged in the lumen of said catheter;
   a drive shaft connected to a distal end of the drive wire to be rotated by the drive wire, the drive shaft being axially movable relative the hollow catheter, the drive shaft having a proximal end and a distal end opposite the proximal end;
   a foldable propeller coupled to the drive shaft, the propeller being movable between a folded position and an unfolded position;
   a proximal housing coupled to the proximal end of the drive shaft;
   a distal housing spaced apart from the proximal housing and coupled to the distal end of the drive shaft;
   several filaments extending between the proximal housing and the distal housing;
   a proximal bearing positioned within the proximal housing; and
   a distal bearing positioned within the distal housing, wherein the drive shaft is journalled between the proximal bearing and the distal bearing, and wherein the propeller is located between the proximal bearing and the distal bearing when in both the folded position and the unfolded position;
   wherein the proximal bearing is connected to the sheath for axial movement with the sheath relative to the drive shaft, and wherein the distal bearing is connected to the drive shaft, whereby axial movement of the sheath relative to the hollow catheter moves the proximal housing toward the distal housing such that said filaments are unfolded to form a cage;
   wherein the drive shaft includes a propeller pin that pivotally couples said propeller to the drive shaft for movement between the folded position, in which the propeller is parallel with the drive shaft, and the unfolded position, in which the propeller is perpendicular to the drive shaft; and
   wherein the drive shaft is surrounded by a sleeve that is connected to the sheath, the sleeve being axially movable with the sheath relative to the drive shaft, said sleeve including actuation pins which are moveable in the axial direction for cooperation with a cam surface of said propeller for unfolding the propeller, whereby a first axial movement of the sheath toward the distal housing unfolds the cage and a second subsequent axial movement of the sheath toward the distal housing causes the actuation pins of the sleeve to engage the cam surface of the propeller to unfold the propeller.

2. The catheter pump according to claim 1, further comprising a spring-loaded bolt arranged for cooperation with cam surfaces of said propeller.

3. The catheter pump according to claim 2, wherein the spring bolt loses its contact with the cam surface of the propeller when the propeller is fully unfolded.

4. The catheter pump according to claim 1, wherein the actuation pins are arranged in such a way that they prevent the propeller from moving over a perpendicular position.

5. The catheter pump according to claim 1 wherein the propeller is locked by the actuation pins when the propeller is fully unfolded.

6. The catheter pump according to claim 1, further comprising:
   a purge system for passing fluid along the hollow catheter to said proximal bearing, for purging and lubrication of said proximal bearing; and
   channel means being arranged in the rotating drive shaft for passing fluid from said proximal bearing to said distal bearing, for purging and lubrication of said distal bearing.

7. The catheter pump according to claim 6, wherein said channel means is arranged between said drive shaft and said sleeve.

8. The catheter pump according to claim 6, wherein said purge system comprises a dedicated hole in said hollow catheter, which hole is used solely for the purpose of passing said fluid from the proximal end of the hollow catheter to the distal end thereof.

9. The catheter pump according to claim 6, wherein said distal bearing is connected to the surrounding space via a lip seal.

10. The catheter pump according to claim 6, wherein said fluid is passing outside the drive wire in said lumen in the direction from the distal end to the proximal end.

11. The catheter pump according to claim 1, wherein the propeller is circumscribed by a girdle.

12. The catheter pump according to claim 11, wherein said girdle comprises an inflatable ring.

* * * * *